United States Patent [19]

Holtkamp

[11] Patent Number: Plant 5,417

[45] Date of Patent: Mar. 12, 1985

[54] AFRICAN VIOLET PLANT NAMED MONIQUE

[75] Inventor: Reinhold Holtkamp, Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 477,689

[22] Filed: Mar. 22, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet plant named Monique having very early and profuse flowering, upright flower stems each carrying 7–10 or more lilac colored flowers, flexible peduncle, and green, attractive leaves.

1 Drawing Figure

The present invention comprises a new and distinct cultivar of African violet plant, botanically known as *Saintpaulia ionantha,* and hereinafter referred to by the cultivar name Monique.

The new cultivar was referred to during the breeding and selection process by the designation C 153/1, and is a product of a planned breeding program.

The new cultivar was originated from a cross made in a controlled breeding program in Isselburg, West Germany. The female, or seed parent was a cultivar designated XIX 4107 Lilac single. The male, or pollen parent was a cultivar designated A 6/1 pink single.

The new cultivar Monique was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Monique has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Monique, which in combination distinguish this African violet as a new and distinct cultivar:

(1) Very early flowering, 5–6 weeks after potting.
(2) Profuse flowering.
(3) Upright flower stems.
(4) Attractive lilac flower color.
(5) Flexible leaves and peduncle
(6) 8–10 flower stems.
(7) Fresh green, attractive leaves.

The accompanying photographic drawing shows a typical specimen plant of the new cultivar. The colors appearing in the photograph are as true as possible with color illustrations of this type.

In the following description, color references are made to The Horticultural Colour Chart (H.C.C.) issued by Wilson Colour Ltd., except where general colors of ordinary significance are referred to. Color values were taken under natural light conditions approximately mid-day in Nashville, Tenn.

Botanical classification: *Saintpaulia ionantha,* Ramat., cv Monique.

Parentage:

*Male parent.*—A 6/1 pink single.

*Female parent.*—XIX 4107 lilac single.

Propagation: The new cultivar holds its distinguishing characteristics through successive propagations by leaf cuttings and by division of shoots.

Plant: From 8 cm. to 10 cm. tall when grown in pots, and approximately 20–25 cm. in diameter when fully grown.

Leaves:

*General form.*—Oval/round.

*Daimeter.*—65–70 mm.

*Texture.*—Velvety, shiny.

*Aspect.*—Slightly hairy.

*Veins.*—Well pronounced, light green, shiny.

*Color (upperside).*—Parsley green 00962.

*Color (underside).*—Purplish red, hairy.

*Petiole.*—Brownish, hairy.

Flowers:

*Buds.*—Bell shape, purplish before opening.

*Sepals.*—5 in number, brown spear shape, hairy. Calyx: Funnel shape, flat. Peduncle: Short, strong, brownish-red, hairy.

*Individual flowers.*—Size: 40 mm. Color: Upper side: Bishops violet 34/1. Underside: Bishops violet 34/2. Borne: One strong upright flower stem, 7–10 or more flowers. Shape: Conventional violet shape, occasionally additional small petals in the center of the flower. Corolla: Compact flower bouquet with long lasting non-dropping flowers. Flowering time: First flowers appear 5–6 weeks after potting; after 8 weeks full flowering saleable plant.

Reproductive organs:

*Anthers.*—Two anthers composed of four cells; sulphur yellow seed capsule pushed slightly through.

*Filaments.*—Violet 36.

*Styles.*—4–6 mm.; base of ovary light green, hairy.

Roots: Normally developed, white and hairy when active; brownish when older.

Disease resistance: Good as experienced to date.

General observations: Monique is a medium size, vigorous growing cultivar. There are 7–10 or more wire-like flower stems, each of which carries 6–9 or more flowers which are violet shaped. The flowers are long-lasting, non-dropping and profuse, and the cultivar flowers continuously after first blooming.

I claim:

1. A new and distinct variety of African violet plant named Monique, as described and illustrated, having early and profuse flowering, upright flower stems each carrying 7–10 or more lilac colored flowers, flexible peduncle and green, attractive leaves.

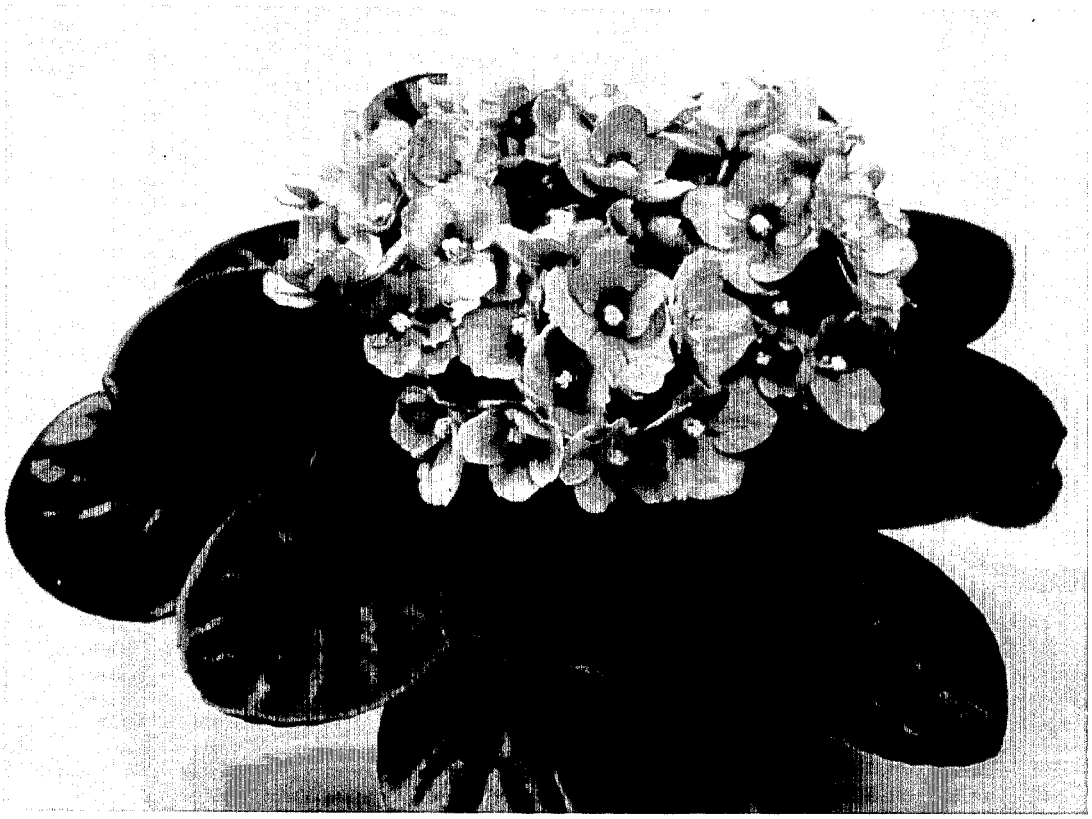

* * * * *